United States Patent [19]

Andersson et al.

[11] Patent Number: 5,739,152
[45] Date of Patent: Apr. 14, 1998

[54] PHARMACEUTICAL EMULSION

[75] Inventors: Kjell Hjalmar Andersson, Fjärås; Eva Kristina Byröd, Mölndal; Anna-Carin Hansson, Göteborg; Margareta Nordlander, Askim; Rolf Christer Westerlund, Mölndal, all of Sweden

[73] Assignee: Astra Aktiebolag, Sodertalje, Sweden

[21] Appl. No.: 364,953

[22] PCT Filed: Nov. 3, 1994

[86] PCT No.: PCT/SE94/01032

§ 371 Date: Dec. 28, 1994

§ 102(e) Date: Dec. 28, 1994

[87] PCT Pub. No.: WO95/13066

PCT Pub. Date: May 18, 1995

[30] Foreign Application Priority Data

Nov. 12, 1993 [SE] Sweden .................. 9303744

[51] Int. Cl.$^6$ .................................. A61K 31/44
[52] U.S. Cl. .................................. 514/356
[58] Field of Search ............... 514/356, 78, 558, 514/943

[56] References Cited

U.S. PATENT DOCUMENTS 4,711,902 12/1987 Serno ........................... 514/356

FOREIGN PATENT DOCUMENTS

0143305A1  6/1985  European Pat. Off. .
3315805A1  11/1984  Germany .
3515335A1  10/1986  Germany .
4217842A1  12/1993  Germany .

OTHER PUBLICATIONS

Seki, et al., *Chemical Abstracts*, vol. 115, p. 479, Abstract No. 78948c (1991).

*Primary Examiner*—Phyllis G. Spivack
*Attorney, Agent, or Firm*—White & Case

[57] ABSTRACT

A pharmaceutical emulsion for intravenous administration is disclosed which comprises
  a) a short acting dihydropyridine compound;
  b) a lipid phase;
  c) an emulsifier and
  d) water or a buffer.

10 Claims, No Drawings

PHARMACEUTICAL EMULSION

This application is a 371 of PCT/SE94/01032 filed Nov. 3, 1994, PUBLISHED AS wo95/13066 mAY 18, 1995.

FIELD OF INVENTION

The present invention relates to emulsions of novel, potent, very short acting, antihypertensive calcium antagonists of the dihydropyridine type with high vascular selecitivity, and to a process for preparing such emulsions. The invention also relates to the use of the emulsion in intravenous administration during surgery and postoperatively in hypertension and for short term treatment of hypertension when oral therapy is not feasible or desirable.

1. Background to the Invention

Steerable blood pressure control is of great importance in many acute clinical situations, e.g. in the majority of patients undergoing cardiac surgery, cerebral surgery, orthopedic surgery or microsurgery. Under such conditions it is often important to rapidly and safely lower blood pressure to a pre-specified level, keeping it there for a pre-determined time, and then rapidly normalizing it again. In these situations it is important to minimize the volumes given to the patient. Therefore it is important to administer a concentrated pharmaceutical preparation.

Short acting dihydropyridines are sparingly soluble in water, but have a moderate to high lipophilicity. There exist today a clear medical need for short acting, steerable antihypertensive drugs for intravenous administration during surgery and postoperatively administered in the form of a reasonably concentrated pharmaceutical preparation with minimal side effects.

2. Prior Art

Emulsions for parenteral nutrition, such as Intralipid®, are well known and have been used for a long time.

There also exist emulsions as drug delivery systems, in the field of dihydropyridines, for treating high blood pressure. In contrast to the present invention these formulations result in long-acting blood pressure effects.

DESCRIPTION OF THE INVENTION

It has now been found that the problems outlined above can be solved by providing an oil-in-water emulsion comprising a) a short acting dihydropyridine compound,
b) a lipid phase,
c) an emulsifier, and
d) water or a buffer.

When dissolved in conventional solutions the short acting dihydropyridine compounds induce rapid and steerable blood pressure reduction in animals. When dissolved as a lipid emulsion the pharmacological effect remains the same as with conventional solutions.

Emulsions of the invention offer much better solubility and/or less side effects of the vehicle and/or better stability than conventional solutions. Oil-in-water emulsions also prevent the lipophilic dihydropyridine compounds from adherence to the plastic infusion sets etc. that are to be used when administrating the compounds.

The emulsions of the invention are useful as dosage forms for short-acting (i.e. half life in plasma less than 30 minutes) antihypertensive dihydropyridines. The emulsions gives as fast release, together with as fast decay, in pharmacological effect as conventional solutions, but the emulsions offer much better solubility properties, and/or less side effects of the vehicle and/or better stability than conventional solutions.

Below is given a detailed description of the invention.

Pharmaceutical material comprises emulsions or freeze dried material from emulsions or concentrates for reconstitution (self-emulsifying systems).

Emulsion comprises:

a) 0.001–20% of short acting dihydropyridine compound b) 1–35% of lipid phase c) emulsifier of 0.01–2 times wt. of (b)

d) 40–99% of water or a buffer

Percentages throughout the specification is expressed as weight/weight.

The short acting dihydropyridine compound is selected from the group consisting of a 1,4-dihydropyridine of the general formula I:

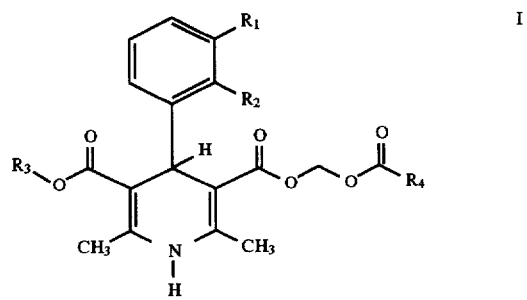

or pharmaceutically acceptable salts therof, wherein $R_1$ and $R_2$ are independently selected from the group consisting of hydrogen, chloro, bromo, nitro, cyano, trifluoromethyl, and $R_3$ and $R_4$ are independently selected from straight or branched lower (1–5 carbon atoms) alkyl groups, and including all optical isomers, provided that when $R_3$ is methyl and $R_4$ is tert.-butyl, then $R_1/R_2$ are not hydrogen/hydrogen, hydrogen/2'-trifluormethyl, 2'-chloro/3'-chloro, and when $R_3$ is methyl and $R_1/R_2$ is hydrogen/3'-nitro, then $R_4$ are not methyl, ethyl, propyl, iso-propyl, tert.-butyl.

These compounds can be prepared from the corresponding, suitably substituted 1,4-dihydropyridine monocarboxylic acid (II) by standard alkylation with acyloxychloromethanes in the presence of base, as outlined below.

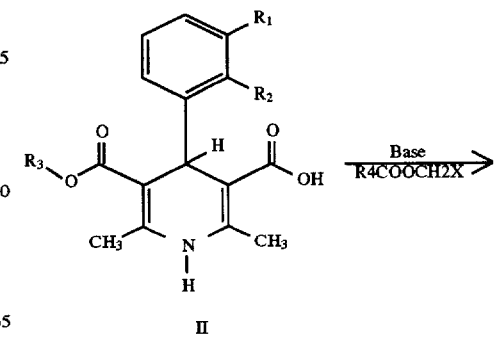

II

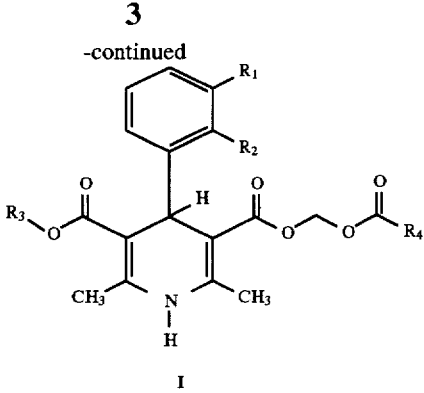

wherein $R_1$–$R_4$ have the same meaning as described above, and base is such as sodium hydride, sodium bicarbonate, triethylamine and X is a standard leaving group such as a halogen atom, tosylate or mesylate. As solvent can a polar aprotic solvent be used, such as dimethylformamide.

The preferred dihydropyridine compounds are:
Acetoxymethyl methyl 4-(2',3'-dichlorophenyl)-2,6-dimethyl-1,4-dihydropyridine-3,5-dicarboxylate
Propionoxymethyl methyl 4-(2',3'-dichlorophenyl)-2,6-dimethyl-1,4-dihydropyridine-3,5-dicarboxylate
Butyroxymethyl methyl 4-(2',3'-dichlorophenyl)-2,6-dimethyl-1,4-dihydropyridine-3,5-dicarboxylate
(4S)-Butyroxymethyl methyl 4-(2',3'-dichlorophenyl)-2,6-dimethyl-1,4-dihydropyridine-3,5-dicarboxylate
iso-Butyroxymethyl methyl 4-(2',3'-dichlorophenyl)-2,6-dimethyl-1,4-dihydropyridine-3,5-dicarboxylate Specially preferred dihydropyridine compounds are
Butyroxymethyl methyl 4-(2',3'-dichlorophenyl)-2,6-dimethyl-1,4-dihydropyridine-3,5-dicarboxylate
(4S)-Butyroxymethyl methyl 4-(2',3'-dichlorophenyl)-2,6-dimethyl-1,4-dyhydropyridine-3,5 -dicarboxylate
(4R)-Butyroxymethyl methyl 4-(2',3'-dichlorophenyl)-2,6-dimethyl-1,4-dihydropyridine-3,5-dicarboxylate Compound A: Acetoxymethyl methyl 4-(2',3'-dichlorophenyl)-2,6-dimethyl-1,4-dihydropyridine-3,5-dicarboxylate To a stirred mixture of 1,4-dihydro-2,6-dimethyl-4-(2',3'-dichorophenyl)-5-carboxymethyl-3-pyridinecarboxylic acid (0.3 g, 0.83 mmol) and sodium bicarbonate (0.14 g, 1.69 mmol)in DMF (15 ml) under nitrogen atmosphere was added chloromethyl acetate (0.137 g, 1.26 mmol). The reaction mixture was heated at 80° C. for 18 h. Workup by evaporation of solvent and addition of water. Extraction with dichloromethane, the extract was dried over sodium sulfate and concentrated. The resulting oil was subjected to flash chromatography [silica gel, dichloromethane—dichloromethane/methanol (9/1) gradient] to give colorless crystals (0.17 g, 48%) mp. 144.5°–147.6° C. $^1$H-NMR (CDCl$_3$): 7.30–7.04 (Ar, 3H); 5.97 (s, 1H); 5.73 (d, J=5.5 Hz, 1H); 5.69 (d, J=5.5 Hz, 1H); 5.46 (s, 1H); 3.6 (s, 3H); 2.32 (s, 3H); 2.30 (s, 3H); 2.03 (s, 3H). $^{13}$C-NMR (CDCl$_3$): 169.64; 167.63; 165.81; 147.46; 146.77; 143.85; 132.86; 131.15; 129.83; 128.31; 126.98; 103.97; 101.89; 78.73; 50.93; 38.45; 20.80; 19.86; 19.26.

Compound B: Propionoxymethyl methyl 4-(2',3'-dichiorophenyl)-2,6-dimethyl-1,4-dihydropyridlne-3,5-dicarboxylate To a stirred mixture of 1,4-dihydro-2,6-dimethyl-4-(2',3'-dichorophenyl)-5-carboxymethyl-3-pyridinecarboxylic acid (5 g,14 mmol) and sodium hydride (0.6 g, 14 mmol) in DMF (25 ml) under nitrogen atmosphere was added chloromethyl propionate (1.71 g, 14 mmol). The reaction mixture was heated at 80° C. for 16 h. Workup by evaporation of solvent and addition of water. Extraction with dichloromethane, the extract was dried over sodium sulfate and concentrated. The resulting yellow crystals was subjected to flash chromatography [silica gel, dichloromethane—dichloromethane/methanol (9/1) gradient] to give pale yellow crystals (2.21 g, 36%), mp. 123.8°–125.5° C. $^1$H-NMR (CDCl$_3$): 7.30–7.03 (Ar, 3H); 5.97 (s, 1H); 5.75 (d, J=5.5 Hz, 1H); 5.72 (d, J=5.5 Hz, 1H); 5.46 (s, 1H); 3.60 (s, 3H); 2.34–2.25 (m, 8H); 1.09 (t, J=7.5 Hz, 3H). $^{13}$C-NMR (CDCl$_3$): 173.11; 167.65; 165.83; 147.47; 146.70; 143.87; 132.86; 131.14; 129.83; 128.30; 126.96; 103.95; 101.94; 78.70; 50.92; 38.45; 27.25; 19.86; 19.25; 8.61.

Compound C: Butyroxymethyl methyl 4-(2',3'-dichlorophenyl)-2,6-dimethyl-1,4-dihydropyridine-3,5-dicarboxylate To a stirred mixture of 1,4-dihydro-2,6-dimethyl-4-(2',3'-dichorophenyl)-5-carboxymethyl-3-pyridinecarboxylic acid (2.62 g, 7.35 mmol) and sodium bicarbonate (1.26 g, 15 mmol) in DMF (130 ml) under nitrogen atmosphere was added chloromethyl butyrate (1.53 g, 11.21 mmol). The reaction mixture was heated at 80° C. for 24 h. Workup by filtration followed by evaporation of solvent. The crude residue was chromatographed on silica gel with 45% ethyl acetate in isooctane. Recrystallization from diisopropylether gave colorless crystals (2.20 g, 66%), mp. 136.2°–138.5° C. $^1$H-NMR (CDCl$_3$): 7.30–7.03 (m, 3H); 5.89 (s, 1H); 5.74 (d, J=5.5 Hz, 1H); 5.70 (d, J=5.5 Hz, 1H); 5.46 (s, 1H); 3.60 (s, 3H); 2.33 (m, 8H); 1.65–1.55 (m, 2H); 0.90 (t, J=7.4 Hz, 3H). $^{13}$C-NMR (CDCl$_3$): 172.25; 167.61; 165.80; 147.43; 146.59; 143.82; 132.89; 131.11; 129.82; 128.30; 126.95; 103.97; 101.99; 78.63; 50.92; 38.49; 35.79; 19.91; 19.30; 18.01; 13.50.

Compound D: (4S)-Butyroxymethyl methyl 4-(2',3'-dichlorophenyl)-2,6-dimethyl-1,4-dihydropyridine-3,5-dicarboxylate To a stirred mixture of (4R)-1,4-dihydro-2,6-dimethyl-4-(2',3'-dichorophenyl)-5-carboxymethyl-3-pyridinecarboxylic acid (2.93 g, 8.23 mmol) and sodium bicarbonate (1.38 g, 16.5 mmol)in DMF (150 ml) under nitrogen atmosphere was added chloromethylbutyrate (1.72 g, 12.6 mmol). The reaction mixture was heated at 80° C. for 17 h. Workup by filtration followed by evaporation of solvent. The crude residue was chromatographed on silica gel with 5% ethylacetate in dichloromethane. Recrystallization from diisopropylether gave colorless crystals (2.62 g, 70%), mp. 128°–129° C. NMR spectral data are identical with the data of the racemate as shown for Compound C. $[\alpha]_D^{20}$=+17.5° (1% in methanol).

Compound E: (4R)-Butyroxymethyl methyl 4-(2',3'-dichlorophenyl)-2,6-dimethyl-1,4-dihydropyridine-3,5-dicarboxylate To a stirred mixture of (4S)-1,4-dihydro-2,6-dimethyl-4-(2',3'-dichorophenyl)-5-carboxymethyl-3-pyridinecarboxylic acid (2.0 g, 5.61 mmol) and sodium bicarbonate (0.96 g, 11.4 mmol) in DMF (100 ml) under nitrogen atmosphere was added chloromethylbutyrate (1.16 g, 8.5 mmol). The reaction mixture was heated at 80° C. for 23 h. Workup by filtration followed by evaporation of solvent. The crude residue was dissolved in dichloromethane and washed with sodium bicarbonatesolution. The organic phase was dried over sodium sulfate and evaporated. Recrystallization first from a mixture of 45% ethylacetate in isooctane followed by diisopropylether gave colorless crystals (1.08 g, 42%), mp. 128°–129° C. NMR spectral data are identical with the data of the racemate as shown for Compound C. $[\alpha]_D^{20}$=–21.5° (1% in methanol).

Compound F: Isobutyroxymethyl methyl 4-(2',3'-dichlorophenyl)-2,6-dimethyl-1,4-dihydropyridlne-3,5-dicarboxylate To a stirred mixture of 1,4-dihydro-2,6-dimethyl-4-(2',3'-dichorophenyl)-5-carboxymethyl-3-pyridinecarboxylic acid (5.11 g, 14 mmol) and sodium bicarbonate (2.39 g, 28 mmol) in DMF (250 ml) under argon atmosphere was added chloromethyl isobutyrate (2.93 g, 21 mmol). The reaction mixture was heated for 80° C. for 18 h. Workup by evaporation of solvent. The crude residue was dissolved in dichloromethane and washed with sodium bicarbonate-solution. The organic layer was dried and evaporated. The residue was chromatographed on silica gel by gradient eluation (dichloromethane to 25% ethyl acetate in dichloromethane). Recrystallization from diisopropylether gave colorless crystals (3.35, 52%), mp. 145° C. $^1$H-NMR (CDCl$_3$): 7.30–7.04 (m, 3H); 5.73 (d, J=5.5 Hz, 1H); 5.71 (d, J=5.5 Hz, 1H); 5.68 (s, 1H); 5.47 (s, 1H); 3.60 (s, 3H); 2.49 (m, 1H); 2.33 (s, 3H); 2.31 (s, 3H); 1.10 (m, 6H). $^{13}$C-NMR (CDCl$_3$): 175.66; 167.62; 165.77; 147.44; 146.47; 143.78; 132.97; 131.24; 129.81; 128.33; 126.93; 103.99; 102.06; 78.89; 50.86; 38.63; 33.69; 19.83; 19.22; 18.55.

The preferred range of short acting dihydropyridine compound is 0.05–1%.

Lipid phases in the emulsion are any pharmaceutically acceptable oil, preferably triglycerides such as soy bean oil, safflower seed oil, olive oil, cottonseed oil, sunflower oil, sesame oil, peanut oil, corn oil, medium chain triglycerides (such as Miglyol® 812 or 810) or triacetin. The lipid phase may also be propylene glycol diesters or monoglycerides (such as acetylareal monoglycerides). The lipid phase can also be a mixture of said ingredients.

The most preferred lipid phase is soy bean oil.

The preferred range of lipid is 10–20%.

Emulsifiers are any pharmaceutically acceptable emulsifier, preferably phospholipids extracted from egg yolk or soy bean, synthetic phosphatidyl cholines or purified phosphatidyl cholines from vegetable origin. Hydrogenated derivatives can also be used, such as phosphatidyl choline hydrogenated (egg) and phosphatidyl choline hydrogenated (soya). Emulsifiers may also be non-ionic surfactants such as poloxamers (for example Poloxamer 188 and 407), poloxamines, polyoxyethylene stearates, polyoxyethylene sorbitan fatty acid esters or sorbitan fatty acid esters. Ionic suffactants may also be used such as cholic acid and deoxycholic acid or surface active derivivatives or salts thereof. The emulsifier can also be a mixture of said ingredients.

The most preferred emulsifier is egg lecithin.

The preferred range of emulsifier is 0.5–4%.

The preferred range of water or buffer is 75–90%.

The emulsion may also contain co-solvents or other solubility enhancers, antioxidants, stabilizers, pH-adjusting agents or tonicity modifying agents, such as glycerol.

Desirable emulsions are a stable systems of small average droplet size of 0.05–1.0 μm and narrow droplet size distribution.

Since the dihydropyridine compounds are sensitive to hydrolysis, oil-in-water emulsions are preferred to conventional water-based solutions in order to get stable dihydropyridine formulations.

The dihydropyridine compounds are also light sensitive and do easily bind to many materials such as plastics. In both these cases the oil-in-water emulsion is a much better vehicle than conventional solutions are.

The emulsion according to the invention can be prepared in the following manner:

The short-acting dihydropyridine compound is dissolved or dispersed in the lipid phase, optionally under heating. The emulsifier is dispersed or dissolved in the water phase (or buffer), optionally together with a tonicity agent or in the lipid phase. The water phase is added to the lipid phase or vice versa. Preferably, the mixture is heated and a coarse emulsion is prepared with a high shear mixer. Finally, the coarse emulsion is processed by a high pressure homogenizer. pH may be adjusted. The emulsion can be filtered before being filed into suitable dosage units, often with nitrogen gassed topspace and preferably the dosage units are autoclaved, to get sterile and stable emulsions.

Therapeutic doses in man are in the range 0.1–100 mg/kg/hour of active substance, preferably 1–20 mg/kg/hour.

WORKING EXAMPLES

The substance was dissolved in the lipid phase, optionally under heating. The emulsifier was dispersed or dissolved in the water phase together with the tonicity agent (i.e. glycerol) by a Polythron PT 1200 high shear mixer. The lipid phase was mixed with the water phase. The mixture was heated to approximately 60° C. and a coarse emulsion was prepared by Polythron PT 1200 high shear mixer. Finally, the coarse emulsion was processed by a high pressure homogenizer (Rannie model minilab type 8.30H or Avestin Emulsiflex 20000-B3) to a free emulsion, with small average droplet size (<0.5 μm) and narrow distribution. The emulsion was filtered (typically 0.45 μm) before being filled into vials. The headspace of each bottle was nitrogen purged prior to stoppering. Optionally the emulsion vials were autoclaved.

The emulsions was characterized physically, such as by microscope, laser diffraction (Coulter LS130), photon correlation spectroscopy (Coulter N4MD), visually and chemically such as by LC and pH-meter. The stability of the emulsions was followed for at least two weeks and up to two months.

| Example 1 | |
|---|---|
| Compound C | 0.001 g |
| soy bean oil | 0.2 g |
| egg lecithin | 0.02 g |
| glycerol | 0.022 g |
| water for injection | to 1 g |
| Example 2 | |
| Compound C | 0.0005 g |
| soy bean oil | 0.1 g |
| egg lecithin | 0.0125 g |
| glycerol | 0.022 g |
| water for injection | to 1 g |
| Example 3 | |
| Compound C | 0.0024 g |
| Miglyol 812 ® | 0.2 g |
| egg lecithin | 0.015 g |
| glycerol | 0.022 g |
| water for injection | to 1 g |

Examples 1–3

One part of each emulsion was autoclaved. Both the autoclaved and the non autoclaved emulsions were studied for 2 months. There were no significant changes in stability during this time, except from a drop in pH in the autoclaved emulsions, which could be avoided by adjusting the pH with sodium hydroxide before autoclaving.

| Example 4 | |
|---|---|
| Compound C | 0.0003 g |
| olive oil | 0.2 g |
| egg lecithin | 0.02 g |
| glycerol | 0.022 g |
| water for injection | to 1 g |

| Example 5 | |
|---|---|
| Compound C | 0.0012 g |
| Miglyol 812 ® | 0.2 g |
| soy bean lecithin | 0.015 g |
| glycerol | 0.022 g |
| water for injection | to 1 g |

| Example 6 | |
|---|---|
| Compound C | 0.0006 g |
| Miglyol 812 ® | 0.1 g |
| egg lecithin | 0.015 g |
| glycerol | 0.022 g |
| water for injection | to 1 g |

| Example 7 | |
|---|---|
| Compound D | 0.0008 g |
| soy bean oil | 0.2 g |
| egg lecithin | 0.02 g |
| glycerol | 0.022 g |
| water for injection | to 1 g |

| Example 8 | |
|---|---|
| Compound E | 0.0007 g |
| soy bean oil | 0.2 g |
| egg lecithin | 0.02 g |
| glycerol | 0.022 g |
| water for injection | to 1 g |

| Example 9 | |
|---|---|
| Compound B | 0.0009 g |
| soy bean oil | 0.2 g |
| egg lecithin | 0.02 g |
| glycerol | 0.022 g |
| water for injection | to 1 g |

| Example 10 | |
|---|---|
| Compound F | 0.0007 g |
| soy bean oil | 0.2 g |
| egg lecithin | 0.02 g |
| glycerol | 0.022 g |
| water for injection | to 1 g |

| Example 11 | |
|---|---|
| Compound A | 0.0007 g |
| soy bean oil | 0.2 g |
| egg lecithin | 0.02 g |
| glycerol | 0.022 g |
| water for injection | to 1 g |

Examples 4–11

The stability of the emulsions was satisfactory for at least two weeks.

Pharmacological properties

The compounds of the invention show short-acting, potent anti-hypertensive effects. The compounds have been dissolved in conventional solutions and in lipid emulsions and the pharmacological effects have been evaluated after intravenous infusion to spontaneously hypertensive rats (SHR). The length of the effect duration was determined by stepwise increasing of infusion rates over 15 minutes, until the mean arterial blood pressure was reduced to 30% of the control level. Upon termination of the infusion, the time required for blood pressure normalization (from 70% to 90% of control level) was determined. The so obtained "recovery times", which are a measure of duration of effect for the two types of dosage forms are given in table 1.

Potency of the drug in the two dosage forms has been measured in hypertensive rats by the mount (nmol/kg) required to stepwise lower arterial blood pressure 20% ($ED_{20}$).

TABLE 1

| | Recovery time (min) | Potency (nmol/kg/min) |
|---|---|---|
| H 324/36 in solutol-solution (n = 6) | 3.4 ± 2.5 | 15.9 ± 5.5 |
| H 324/36 in o/w emulsion (n = 5) | 3.5 ± 3.2 | 22.5 ± 4.6 |

From these experiments it was concluded that dissolving the test compound(s) in the lipid emulsion did not interfere with the pharmacological provide of the compound(s). Thus, neither potency nor the rapid metabolism of the test compound was affected since potency values and recovery times were similar when the compound(s) were dissolved in a conventional solution (solutol 1:20 w/w) or in a lipid emulsion. Consequently, the administered volume can be kept at a minimum, which is a substantal therapeutic advantage.

We claim:

1. A pharmaceutical formulation which is an emulsion for intravenous administration and which comprises
   a) a short-acting dihydropyridine compound having a half-life in plasma of less than 30 minutes;
   b) a lipid phase;
   c) an emulsifier; and
   d) water or a buffer.

2. A formulation according to claim 1, wherein the short-acting dihydropyridine compound is selected from the group consisting of 1,4-dihyro-pyridine compounds of the formula I:

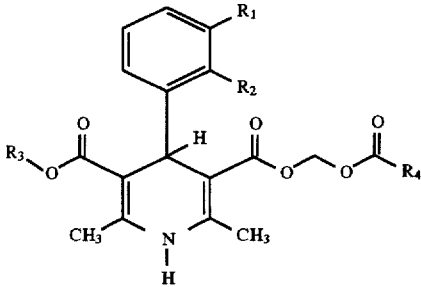

or a pharmaceutically acceptable salt or a stereoisomer thereof, wherein $R_1$ and $R_2$ are independently selected from the group consisting of hydrogen, chloro, bromo, nitro, cyano and trifluoromethyl, and $R_3$ and $R_4$ are independently selected from straight or branched lower (1–5 carbon atoms) alkyl groups, provided that when $R_3$ is methyl and $R_4$ is tert.-butyl, then $R_1/R_2$ are not hydrogen/hydrogen, hydrogen/2'-trifluoromethyl or 2'-chloro/3'-chloro, and when $R_3$ is methyl and $R_1/R_2$ are hydrogen/3'-nitro, then $R_4$ is not methyl, ethyl, propyl, iso-propyl or tert.-butyl.

3. A formulation according to claim 1, wherein the short-acting dihydropyridine compound is selected from the group consisting of
   Acetoxymethyl methyl 4-(2',3'-dichlorophenyl)-2,6-dimethyl-1,4-dihydropyridine-3,5-dicarboxylate;
   Propionoxymethyl methyl 4-(2',3'-dichlorophenyl)-2,6-dimethyl-1,4-dihydropyridine-3,5-dicarboxylate;
   Butyroxymethyl methyl 4-(2',3'-dichlorophenyl)-2,6-dimethyl-1,4-dihydropyridine-3,5-dicarboxylate;

(4S)-Butyroxymethyl methyl 4-(2',3'-dichlorophenyl)-2,6-dimethyl-1,4-dihydropyridine-3,5-dicarboxylate;

(4R)-Butyroxymethyl methyl 4-(2',3'-dichlorophenyl)-2,6-dimethyl-1,4-dihydropyridine-3,5-dicarboxylate and iso-Butyroxymethyl methyl 4-(2',3'-dichlorophenyl)-2,6-dimethyl-1,4-dihydropyridine-3,5-dicarboxylate.

4. A formulation according to claim 1, wherein the short-acting dihydropyridine compound is present in an amount of 0.001–20 per cent by weight of the entire emulsion weight.

5. A formulation according to claim 1, wherein the lipid phase is selected from the group consisting of triglycerides.

6. A formulation according to claim 1, wherein the lipid phase is present in an amount of 1–35 per cent by weight of the entire emulsion weight.

7. A formulation according to claim 1, wherein the emulsifier is a phospholipid.

8. A formulation according to claim 1, wherein the emulsifier is present in an amount of 0.01–2 times by weight of the amount of the lipid phase.

9. A method for short-term lowering of the blood pressure during surgery and postoperatively in a patient whereby a therapeutically active amount of a formulation according to claim 1 is administered intravenously to the patient.

10. A pharmaceutical formulation for use in the short-term lowering of blood pressure in a patient in need thereof comprising a) a short acting dihydropyridine compound having a half-life in plasma of less than 30 minutes;

b) a lipid phase;

c) an emulsifier; and d) water or a buffer.

* * * * *

UNITED STATES PATENT AND TRADEMARK OFFICE
CERTIFICATE OF CORRECTION

PATENT NO. : 5,739,152
DATED : April 14, 1998
INVENTOR(S) : Andersson et al.

It is certified that error appears in the above-indentified patent and that said Letters Patent is hereby corrected as shown below:

In column 8, line 34 (Claim 2), change "-dihyro" to -- -dihydro--.

Signed and Sealed this

Twenty-second Day of June, 1999

Attest:

Q. TODD DICKINSON

*Attesting Officer*  *Acting Commissioner of Patents and Trademarks*